United States Patent [19]

Rafelson

[11] Patent Number: 4,553,538
[45] Date of Patent: Nov. 19, 1985

[54] ENDOSCOPIC PILLOW COVERING WITH HIGH ABSORBENCY CHARACTERISTICS

[76] Inventor: Stephen Rafelson, 20 Stratford La., Mount Laurel, N.J. 08054

[21] Appl. No.: 559,422

[22] Filed: Dec. 8, 1983

[51] Int. Cl.$^4$ ............................................. A61B 19/06
[52] U.S. Cl. ................................................ 128/132 D
[58] Field of Search ............... 128/132 D, 137 D, 1 R

[56] References Cited

U.S. PATENT DOCUMENTS

| 27,710 | 7/1873 | Melger | 128/132 D |
|---|---|---|---|
| 3,799,161 | 3/1974 | Collins | 128/132 D |
| 3,881,474 | 5/1975 | Kazewinski | 128/132 D |
| 3,998,221 | 12/1976 | Collins | 128/132 D |
| 4,040,418 | 8/1977 | Collins | 128/132 D |
| 4,051,845 | 10/1977 | Collins | 128/132 D |
| 4,476,860 | 10/1984 | Collins et al. | 128/132 D |

Primary Examiner—C. Fred Rosenbaum
Assistant Examiner—Christa K. Scott
Attorney, Agent, or Firm—Fleit, Jacobson, Cohn & Price

[57] ABSTRACT

The present invention is used during an upper gastrointestinal endoscopic procedure with the patient in the left lateral decubitus position. A disposable or nondisposable pillow case or covering extension section is positioned below the patient's mouth. The covering and extension section absorbs any salivary or gastric secretions. In addition, loops or pockets are positioned on the covering or extended area to hold a suction catheter during the endoscopic examination. A suction catheter may be held by attachment to a loop or pocket on the extension section of the pillow covering or may be held on the extension section, near the patient, when the catheter is not in use. The absorbent extended area of the pillow covering employs a plastic layer to further protect the surface below the extended covering area.

21 Claims, 10 Drawing Figures

ENDOSCOPIC PILLOW COVERING WITH HIGH ABSORBENCY CHARACTERISTICS

BACKGROUND OF THE INVENTION

Routine endoscopy of the upper gastrointestinal tract requires that the oral cavity be kept free of secretions in order to prevent aspiration or hypoxia. Presently there are no devices which enable the physician, during endoscopy, to have easy access to the catheter; therefore, the catheter is often temporarily placed in a nurse's pocket, in a stretcher's intravenous pole receptacle, or under a patient's pillow.

It is a common practice for the individual patient to require a clean towel or disposable towelette beneath or near the left side of the face to absorb the secretions which are expectorated before suction can remove them. This leads to additional expense and is cost ineffective. It was because of the significant limitations of current routine endoscopic management of the oropharynx that the current device was conceived.

Finally, the presence of a multitude of interventions both therapeutic and diagnostic during endoscopy of the gastrointestinal tract has led to a proliferation of accessories, some of which are not within easy reach, and until now could not in some circumstances be held or anchored to the bedside pillow covering.

SUMMARY OF THE INVENTION

By the present invention, a suction catheter or endoscopic accessory is positioned by an anchor receptacle either on an extension of a pillow case or an extension of a pillow covering or directly on a pillow case or covering. The head surface portion of the case or covering and an extended portion beyond the case or covering are of a highly absorbent material, being either disposable or nondisposable. The extension portion is capable of being separated from the pillow coverings and is removably secured to a pillow, a pillow case or a pillow covering by snaps or velcro patches. In other embodiments, the extension portion is permanently attached to the case or covering.

The covering for this pillow is made disposable or nondisposable, and is fitted with a loop or pocket-shaped anchor to hold a curved or straight suction catheter or other suitably shaped endoscopic instruments or accessories closer to the patient's bedside than is presently possible within easy access for the treating physician.

BRIEF DESCRIPTION OF THE DRAWINGS

The invention will be more readily understood with reference to the accompanying drawings.

DETAILED DESCRIPTION OF THE DRAWINGS

Upper gastrointestinal endoscopy is carried out with the patient in the left lateral decubitus position. Routinely a pillow or cushion is used to support the head and maintain the axial skeleton in a horizontal plane. It is the purpose of the present invention to cover all or some of the surface of the patient's pillow providing for partial or complete protection of the underlying ordinary linen or permanent covering material of the pillow/cushion. The cover also serves to absorb secretions emanating from the patient's mouth and not suctioned in time by the bedside suctioning instruments, that are routinely available but are often not within easy reach. By virtue of anchors to be described later, the suctioning catheters and endoscopic instruments acquire greater proximity to the endoscopic examination activity.

This convenience is of great importance to the patient since multiple measurements, body positionings and interventions are being carried out simultaneously. Modern therapeutic and diagnostic endoscopy requires swift and efficient techniques to provide for optimal patient safety and comfort. The interventions and measurements being done in addition to the observations through the fiberscope include biopsy, cytology, polyp and foreign body removal, laser therapy of bleeding ulcers and diagnostic and surgical techniques involving the bile and pancreatic ducts.

Yet while these endoscopic operative procedures are being carried out, the gastroenterologist and the nurse assistant must also monitor the vital signs of the patient and his overall general appearance. It follows that it is of great importance to ease the handling of endoscopic accessories and one role of the present invention is to hold certain forceps, brushes, cannulas, and injectors closer to the working area of the nurse and doctor than would otherwise be the case. The attachment of these devices and suction catheters would occur by virtue of their particular shape, being anchored to a firmly secured loop or pocket or adhesive material like velcro located on the pillow/surface covering.

The present invention involves a top surface covering or a surrounding pillow case for an ordinary pillow or a pillow designed for endoscopy and is composed of either a non-disposable material such as launderable cotton or a polyester-cotton mixture, or of a disposable material used as a pillow case or pillow covering for the top surface of a pillow. The disposable material may be an absorbent soft and strong paper, a paper/cotton mixture or a water resistant thin plastic layer sandwiched between two absorbent layers of paper or a plastic layer serving as a backing surface for an absorbent paper or a paper/cotton mixture.

Figure 9:
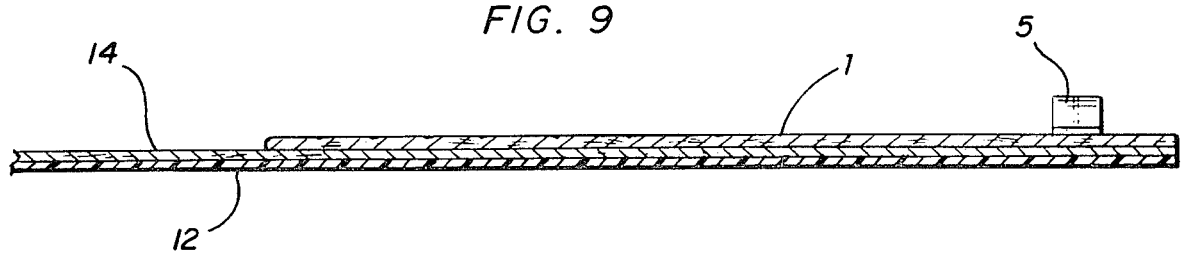
FIG. 9 is a side view of a plastic-paper pillow covering.
Figure 10:
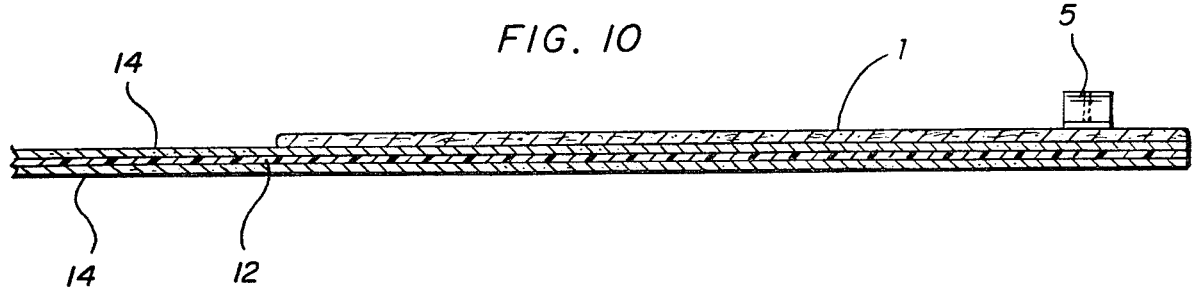
FIG. 10 is a side view of a paper-plastic-paper pillow covering.

In a preferred embodiment, the plastic layer between the two layers or covering one outer absorbent surface, covers approximately 50–100% of the pillow cover and the same amount of the top surface of a pillow case as shown in FIGS. 9 and 10. The 50% minimum portion of plastic layer 12 is located in the area of the pillow covering or pillow case underneath the patient's head. The additional area lined or covered with the plastic middle layer, up to the 100% coverage, is in the area towards the rear and behind the patient's head. The plastic layer is secured between the two absorbent layers by glueing or stitching the outer edges.

The pillow case or pillow covering has an extended edge 1 preferably in the approximate shape of a rectangle or possibly shaped as a hemicircle, hemioval or hemiellipse, with the width being approximately one-half the length to soak up salivary secretions which escape from the patient's mouth prior to and during the endoscopic treatment. In addition there are fabric loops or pocket anchors which may be made of cotton, nylon or other synthetic materials or velcro, permanently attached to either the extended edge, the pillow covering or the pillow case to provide attachment for compatible curved or straight orophyaryngeal suction catheters, endoscopic accessories or accessory holders used in an endoscopic procedure. The loops or pockets in the disposable embodiment are composed of paper or plastic attached by stitching, glueing or adhesive backing.

Figure 5:
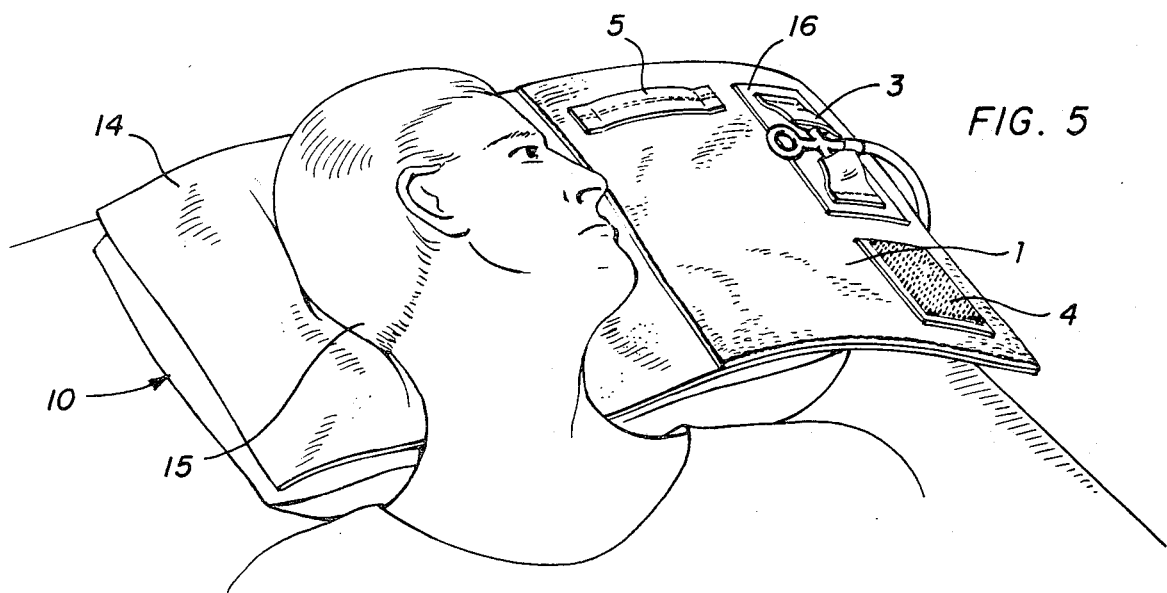
FIG. 5 is an overhead perspective view of a patient positioned for medical treatment.
Figure 8:
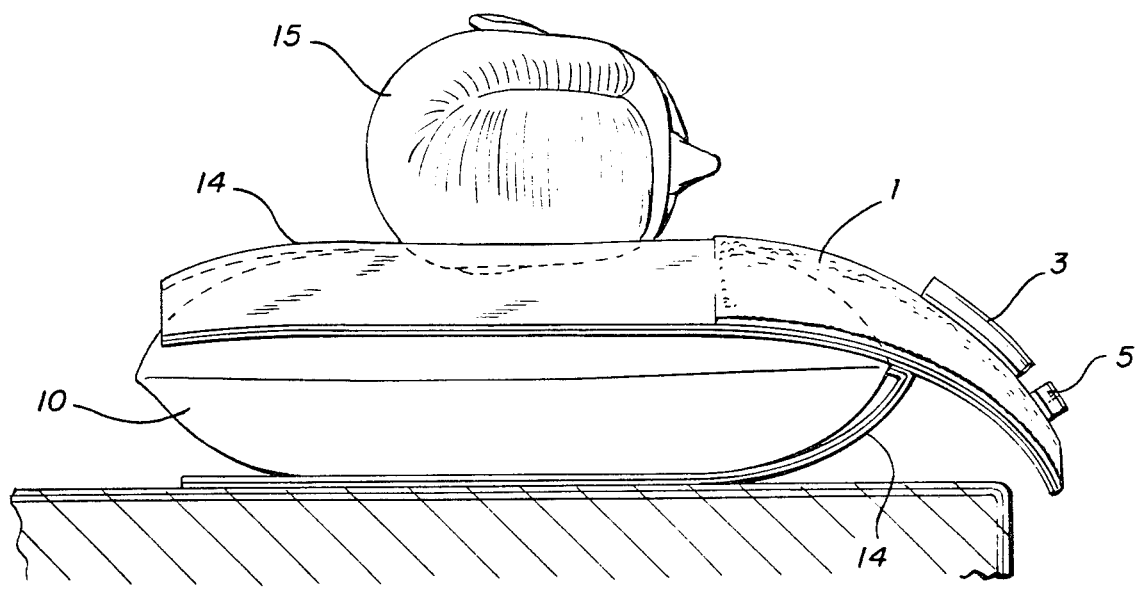
FIG. 8 is a side view of a patient positioned for medical treatment.

It is possible to hold the catheter or operating instruments/accessories closer to the patient's bedside and oral cavity, as shown in FIGS. 5 and 8, than is presently possible, due to the compatible catheters having corresponding attachment devices for securing to the anchors of the pillow case, covering and extended edges such as pen clips, alligator clips or velcro patches or appropriately shaped pockets for insertion of an instrument with resultant suspension.

Similarly snaps 2, loops 5, pockets 3, or velcro patches 4 are located near an area of the casing located beneath the patient's mouth such that a clip for accessories and/or a suction catheter retainer may be attached and removed without difficulty.

The anchor receptacle is composed of a simple loop or narrow pocket, fabricated of cotton, nylon or like material, paper, plastic or a velcro patch, the latter enabling a suction catheter with a receiving velcro patch, or any other compatible material also adherent to velcro, to adhere to the pillow case or covering extension section. The loop, pocket or patch are stitched or glued to the covering, case or extended area.

Figure 6:
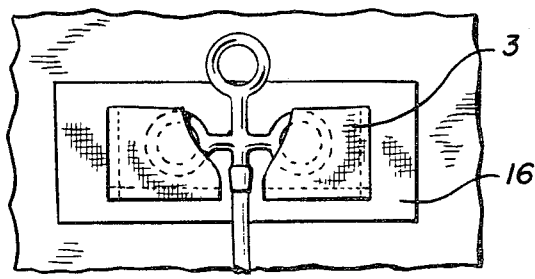
FIG. 6 is a view of an anchor pocket holding an endoscopic accessory.
Figure 7:
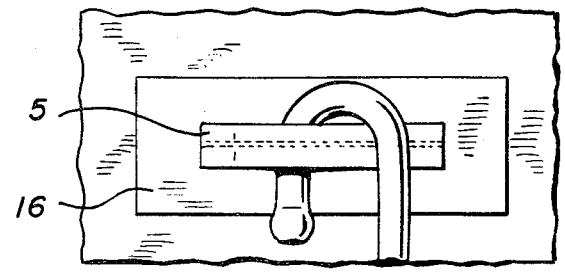
FIG. 7 is a view of an anchor loop holding an endoscopic accessory.

An adhesive backed applique 16, as shown in FIGS. 5, 6 and 7, containing plastic or paper anchors may also be situated at or near the perimeter of the absorbent extended edge of the pillow covering/case. Having the adhesive backed anchor in an L-shape configuration offers two edges for attaching the suction catheter tubing when positioned at the corners of the absorbent covering. In addition, the extended edge 1 of the pillow case 7 or covering 6 closest to the patient's mouth is composed of thick and absorbent material shown in FIG. 8, such as cotton terry, absorbent paper, cotton blends but not necessarily limited to these materials to provide absorption of secretions without ruining the underlying pillow and sheets.

The extended edge 1 segment of absorbent material beneath the patient's head allows absorption of the saliva and gastric secretions brought up involuntarily during the diagnostic procedure. The absorbent material may cover the entire surface of the covering and may vary in thickness, depending on personal or professional preferences. The length of the extended edge 1 segment is as wide as the patient's pillow and the width of the extended edge 1 extends beyond the covering surface material of the pillow in the form of an extension flap, forming a self-contained towel integrated with or separable from the pillow case or pillow covering. The snaps, fabric or paper pockets or loops (fabric, velcro, paper or plastic), serving as anchor receptacles on the surface of the covering or casing and the extension, allow acceptance of accessories with or without clips (not shown) for attachment of frequently used endoscopic accessories such as biopsy forceps, cytology brushes, syringes, suction catheters, diathermic snare/cautery devices, to mention just a few. These implements should be accessable to the treating physician in the eventuality that their use is required. A clip or holder on the accessories or catheter allows attachment to the anchors. Thus, the anchors are positioned to hold the instruments during endoscopy and to keep the instruments proximal to the patient and physician. This frees the physician and nurse to concentrate their efforts on the patient.

Figure 1:
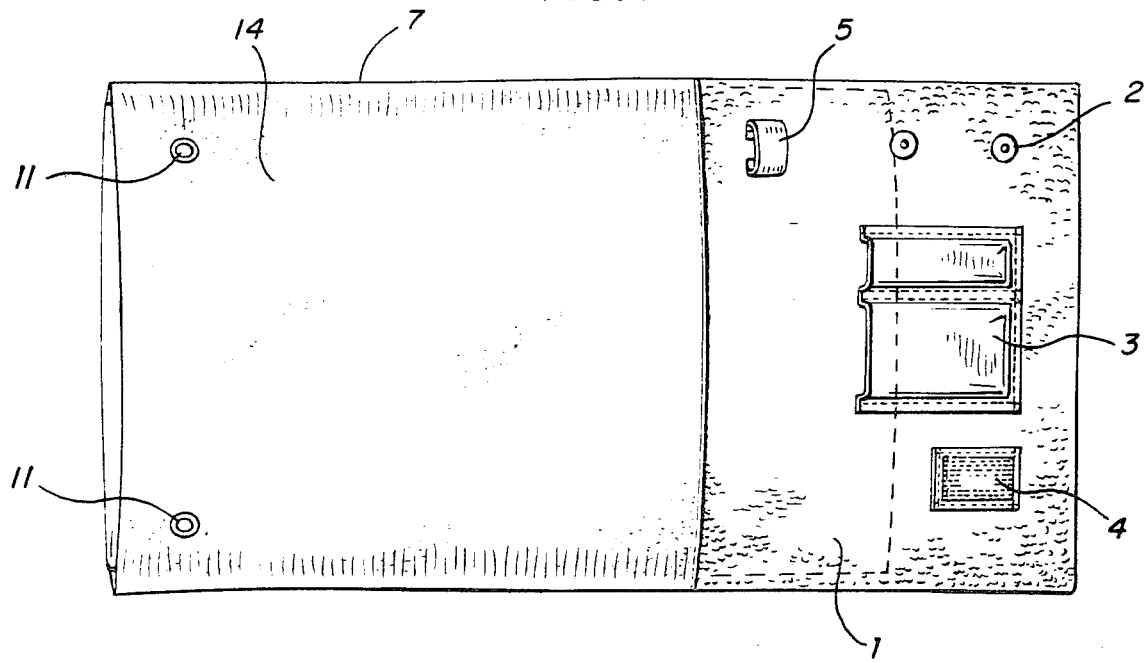
FIG. 1 is an overhead view of a pillow case with an extension section.
Figure 2:
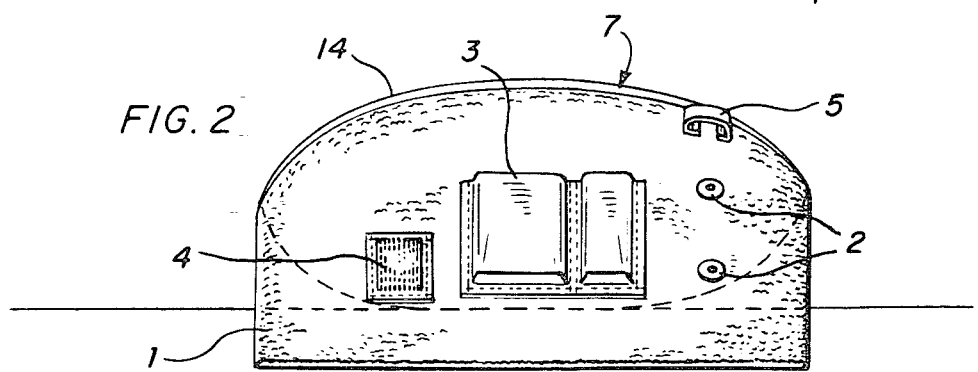
FIG. 2 is an end view of the pillow case and an extension as shown in FIG. 1.
Figure 3:
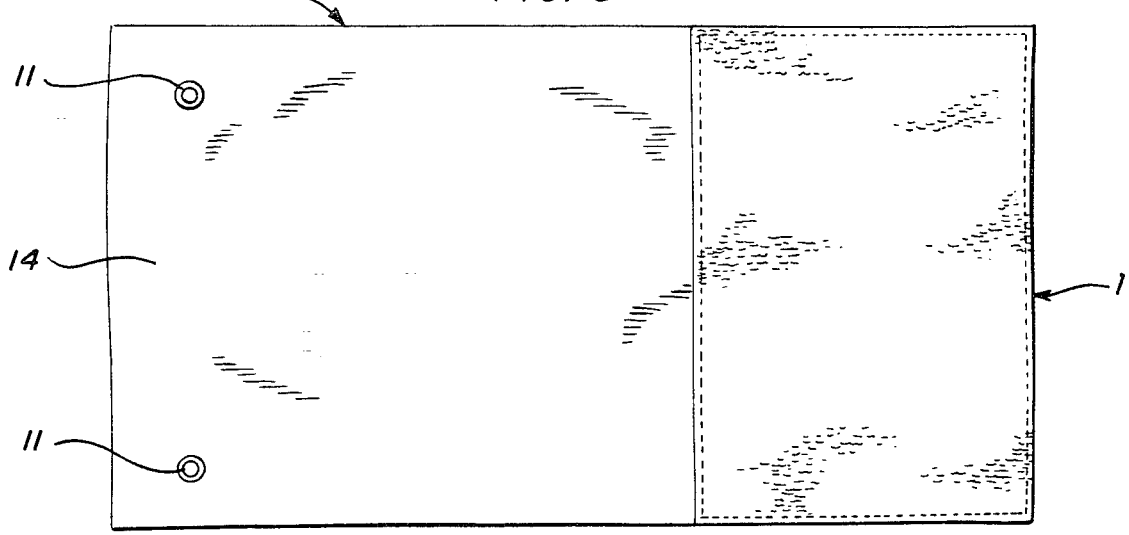
FIG. 3 is an overhead view of a pillow cover with an extension section.

FIGS. 1, 2 and 3 illustrate a combined pillow case 7 or covering 6 which is composed of an absorbent, soft material with, in certain embodiments, a thicker and more absorbent extended edge 1 portion, allowing the absorption of secretions coming from the patient's mouth during a gastrointestinal endoscopic procedure. The cover 6 or case 7 is secured to the pillow 10 by snaps 11 as shown in FIGS. 1 and 3. The snaps 11 are located on the pillow to receive complementary fitting portions on the cover or the case. Sufficient snaps are provided to hold the cover or case still during an endoscopic procedure. Snaps 8 are also provided on the pillow case for securing the extended edge 1 to the pillow when the extended edge contains anchor receptacles, loops, pockets, etc. to hold accessories, with complementary fitting snaps on the extended edge. The extended edge also may be stitched or glued to or simply be an extension, of unitary construction, with the cover 6 or case 7. Velcro may be substituted for the snaps, stitching or glueing.

The catheter contains a ball pen type clip or velcro adhesive material which is secured to the catheter in order to hold the catheter onto the anchor located on the pillow covering. A catheter may have sufficient curvature at a distal end to be easily held by a loop or pocket-type receptacle on the pillow covering shown in FIG. 7. The anchors are situated in an area in front of the patient's mouth on the extended edge 1 of the case 6 or covering 7 but usually, in a preferred embodiment, at the perimeter or within inches of the perimeter of the covering rather than close to the center portion. The exact location varies, depending upon individual preferences, and is deleted on those coverings having some other form of accessory attachment such as snaps 2, that allow direct attachment of a suction catheter with a corresponding attachment snap rather than with a clip attached to the catheter or other endoscopic instruments. In a preferred embodiment, the anchors are located on the extended edge 1 nearer the perimeter than the center position.

In an alternate embodiment, the anchor receptacles which are at least one of the following: a fabric, paper or plastic loop; fabric, paper, velcro or plastic pocket; velcro patches or loops; or snaps attached to the case perimeter, covering perimeter or extended edge and are of a contrasting color to that of a white case, covering or extended edge area. This allows for ease of removal and attachment of compatible suction catheters in dimly lit rooms, which is often the case with endoscopic procedures. A white or colored anchor is secured to the anchor holding area of a covering by a contrasting color stitching or seaming for ease in locating the anchor, as well as for reinforcing and supporting the anchor while being pulled by the suction catheter and connective tubing.

Adhesive backed plastic or paper anchors or adhesive backed appliques with integral plastic or paper anchors may be located on the disposable pillow coverings.

Figure 4:
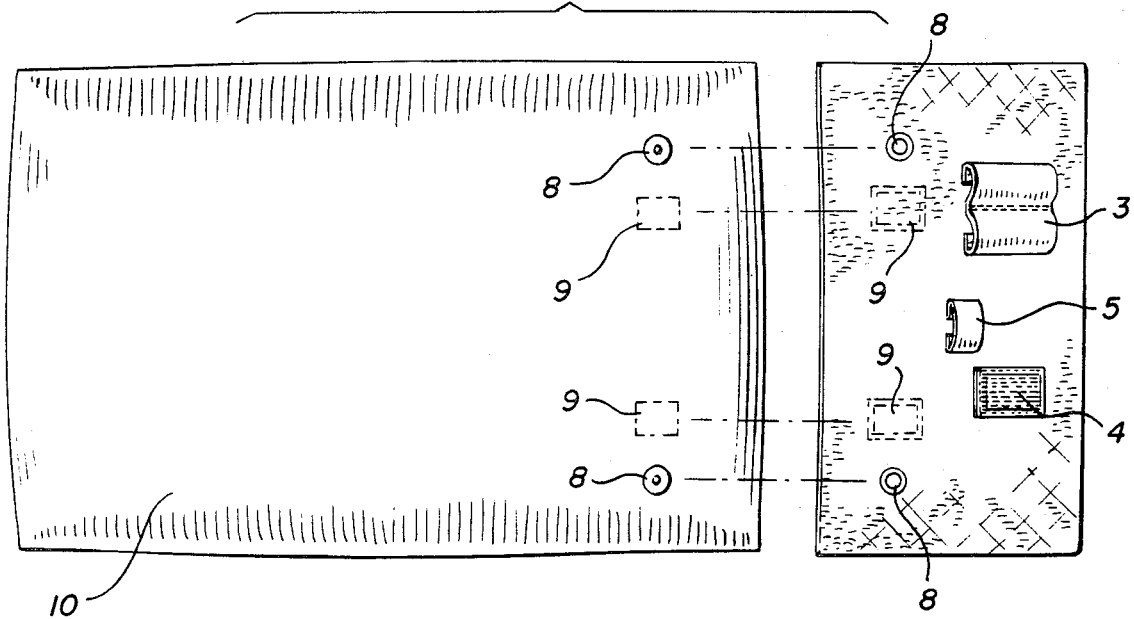
FIG. 4 is an overhead view of a removable extension section.

The pillow covering 6 may not completely encompass the pillow, as would occur with pillow case 7, as shown in FIG. 4. The absorbent disposable or nondisposable pillow covering covers only the top surface of the pillow upon which the patient's face would rest. The absorbent nature of the covering is effective in absorbing the secretions of the patient 15.

The absorbent extended edge 1 extends beyond the pillow covering surface such that it forms a flap that is contiguous with or secured directly by stitching or glue to a pillow as shown in FIG. 4. This is in contrast to the combined use of an extended edge with a pillow case or pillow covering wherein the extended edge is secured by velcro 9 or snaps 8 to the case or cover shown in FIG. 4. The anchors may all be located on the absorbent extension edge near the patient's mouth (FIG. 1) rather than on the thinner pillow covering 14 material which is shown in FIGS. 1 through 3, 5 and 8 through 10. The anchors consist of at least one of the following: snaps, velcro patches, pockets (fabric, paper, plastic, and velcro), and loops (plastic, paper, fabric, velcro).

Snaps 8 or velcro patches 9 secure the extended edge to the pillow for ease of attachment and removal. The present invention provides hygienic covering surfaces, with absorbent towel characteristics, with an extended absorbent edge permanently secured to a pillow case or covering or as a removably attached absorbent extended absorbent edge securable to a pillow and having anchors acting as catheter holders or endoscopic accessory holders.

While a preferred embodiment of the invention has been described using specific material, such description is for illustrative purposes only, and it is to be understood that changes and variations may be made without departing from the spirit and scope of the claimed invention.

I claim:

1. A covering for a pillow adapted to be located beneath a patient's head and mouth used in conjunction with medical instruments during endoscopy of the upper gastrointestinal tract, said covering comprising:
    an absorbent extended edge of a pillow covering adapted to extend beyond the perimeter of a pillow and adapted for placement beneath a patient's mouth; and
    means for anchoring medical instruments to said pillow covering during a medical procedure performed upon said patient.

2. A covering as described in claim 1, wherein said means for anchoring medical instruments comprises at least one of a snap, a loop, a pocket and a velcro patch.

3. A covering as described in claim 2, wherein said means for anchoring is located on said absorbent extended edge.

4. A covering as described in claim 1, wherein said extended edge includes means to permit separation from said pillow covering and is adapted to permit reattachment to said pillow covering.

5. A covering as described in claim 1, wherein said pillow covering is adapted to cover only an exposed surface of said pillow.

6. A covering as described in claim 1, wherein said covering is adapted to encase said pillow.

7. A covering as described in claim 1, wherein said absorbent extended edge contains two paper layers with a plastic layer sandwiched between said two paper layers.

8. A covering as described in claim 1, wherein said pillow covering contains contrasting colored means for anchoring.

9. A covering as described in claim 1, wherein said pillow covering contains adhesive backed means for anchoring.

10. A covering as described in claim 1, wherein said pillow covering possesses high absorbency characteristics over its entire surface.

11. A covering as described in claim 1, wherein said absorbent extended edge is made of a disposable material.

12. A covering as described in claim 11, wherein said disposable material is paper.

13. A covering as described in claim 11, wherein said disposable material is a paper-cotton mixture.

14. A covering as described in claim 1, wherein said absorbent extended edge is made of a non-disposable material.

15. A covering as described in claim 14, wherein said non-disposable material is cotton.

16. A covering as described in claim 14, wherein said non-disposable material is a polyester-cotton mixture.

17. A covering as described in claim 4, wherein said means to permit separation includes at least one of a snap and a velcro patch.

18. A covering as described in claim 1, wherein said anchoring means includes at least one of a loop, velcro patches and a pocket-shaped anchor fitted on said pillow covering.

19. A covering as described in claim 18, wherein said anchoring means is made of at least one of cotton and nylon.

20. A covering as described in claim 18, wherein said anchoring means is made of at least one of paper and plastic.

21. A covering as described in claim 20, wherein said anchoring means includes adhesive backed appliques.

* * * * *